United States Patent
Kim et al.

(10) Patent No.: US 11,076,924 B2
(45) Date of Patent: Aug. 3, 2021

(54) STEERABLE SURGICAL ROBOTIC SYSTEM

(71) Applicants: XCATH, INC., Houston, TX (US); THE BOARD OF REGENTS OF THE UNIVERSITY OF TEXAS SYSTEM, Austin, TX (US)

(72) Inventors: Daniel H. Kim, Houston, TX (US); Dong Suk Shin, Houston, TX (US); Taeho Jang, Houston, TX (US); Yongman Park, Houston, TX (US); Jeihan Lee, Houston, TX (US); Hongmin Kim, Houston, TX (US); Kihoon Nam, Houston, TX (US); Jaeyeon Lee, Houston, TX (US); Viljar Palmre, Pearland, TX (US); Younghee Shim, Houston, TX (US); Bhavik Patel, Houston, TX (US)

(73) Assignees: THE BOARD OF REGENTS OF THE UNIVERSITY OF TEXAS SYSTEM, Austin, TX (US); XCATH, INC., Houston, TX (US)

( * ) Notice: Subject to any disclaimer, the term of this patent is extended or adjusted under 35 U.S.C. 154(b) by 0 days.

(21) Appl. No.: 16/624,429

(22) PCT Filed: Dec. 20, 2018

(86) PCT No.: PCT/US2018/066811
§ 371 (c)(1),
(2) Date: Dec. 19, 2019

(87) PCT Pub. No.: WO2019/133438
PCT Pub. Date: Jul. 4, 2019

(65) Prior Publication Data
US 2020/0197111 A1 Jun. 25, 2020

Related U.S. Application Data

(60) Provisional application No. 62/612,233, filed on Dec. 29, 2017.

(51) Int. Cl.
*A61B 34/30* (2016.01)
*A61M 25/01* (2006.01)
*A61M 25/09* (2006.01)

(52) U.S. Cl.
CPC ......... *A61B 34/30* (2016.02); *A61M 25/0158* (2013.01); *A61M 25/09041* (2013.01);
(Continued)

(58) Field of Classification Search
CPC .............. A61B 34/30; A61B 2034/301; A61B 2034/302; A61B 2034/303;
(Continued)

(56) References Cited

U.S. PATENT DOCUMENTS 6,514,237 B1 2/2003 Maseda
6,679,836 B2 1/2004 Couvillon, Jr.
(Continued)

FOREIGN PATENT DOCUMENTS

JP 2009-527344 A 7/2009
JP 2011519678 A 7/2011
(Continued)

OTHER PUBLICATIONS

PCT International Search Report and Written Opinion for PCT/US2018/066811, dated Apr. 16, 2019.
(Continued)

*Primary Examiner* — Melanie R Tyson
*Assistant Examiner* — Chima U Igboko
(74) *Attorney, Agent, or Firm* — Patterson + Sheridan, LLP

(57) ABSTRACT

Provided herein as a steerable surgical robotic system for positioning a catheter comprising a sheath and a guidewire within a patient body, including a sheath driver configured to advance and retract a sheath having a hollow interior along a sheath advance and retract path extending therein, a
(Continued)

guidewire driver configured to advance and retract a guidewire along a guidewire advance and retract path extending therein, wherein each of the sheath advance and retract path and the guidewire advance and retract path extend between pairs of rollers in the respective sheath and roller drivers, and the paths are parallel to each another.

7 Claims, 10 Drawing Sheets

(52) U.S. Cl.
CPC ............ *A61B 2034/301* (2016.02); *A61M 2025/09175* (2013.01)

(58) Field of Classification Search
CPC ...... A61B 2034/304; A61M 25/09041; A61M 25/0158; A61M 25/0905; A61M 2025/09175; A61M 2025/09116
USPC .......................................................... 606/108
See application file for complete search history.

(56) References Cited

U.S. PATENT DOCUMENTS

| | | | |
|---|---|---|---|
| 6,936,003 B2 | 8/2005 | Iddan | |
| 7,534,242 B2* | 5/2009 | Buehlmann | A61B 18/1492 606/41 |
| 7,615,042 B2 | 11/2009 | Beyar et al. | |
| 7,837,615 B2 | 11/2010 | Le et al. | |
| 7,972,298 B2 | 7/2011 | Wallace et al. | |
| 8,114,032 B2 | 2/2012 | Ferry et al. | |
| 8,388,556 B2 | 3/2013 | Wallace et al. | |
| 8,790,297 B2 | 7/2014 | Bromander et al. | |
| 2006/0084945 A1 | 4/2006 | Moll et al. | |
| 2006/0146010 A1 | 7/2006 | Schneider | |
| 2008/0243030 A1 | 10/2008 | Seibel et al. | |
| 2010/0069833 A1* | 3/2010 | Wenderow | A61B 90/98 604/95.01 |
| 2012/0022405 A1 | 1/2012 | Wallace et al. | |
| 2012/0071752 A1* | 3/2012 | Sewell | A61B 34/74 600/424 |
| 2013/0035537 A1* | 2/2013 | Wallace | A61B 34/30 600/8 |
| 2013/0231678 A1 | 9/2013 | Wenderow et al. | |
| 2014/0081204 A1 | 3/2014 | Cohen et al. | |
| 2016/0235946 A1 | 8/2016 | Lewis et al. | |
| 2016/0338783 A1 | 11/2016 | Romo et al. | |

FOREIGN PATENT DOCUMENTS

| | | |
|---|---|---|
| WO | 2015-057821 A1 | 4/2015 |
| WO | 2017136729 A1 | 8/2017 |

OTHER PUBLICATIONS

Korean Patent Application No. 10-2019-7034617, Notice of Preliminary Rejection dated Jan. 23, 2020, 12 pages.
Taiwan Patent Application No. 107146562, Examination Opinion and Search Report dated Sep. 23, 2019, 4 pages.
Canadian Patent Application No. 3,063,103, Office Action dated May 11, 2020, 4 pages.
Korean Office Action dated May 14, 2020, for Korean Patent Application No. 10-2019-7034617.
Japanese Patent Application No. 2019-563084, Notice of Reasons for Rejection dated Sep. 1, 2020, 6 pages.
Korean Patent Application No. 10-2019-7034617, Final Office Action dated Sep. 25, 2020 with English translation, 8 pages.
European Patent Application No. 18896333.4, extended European search report dated Dec. 4, 2020, 10 pages.

* cited by examiner

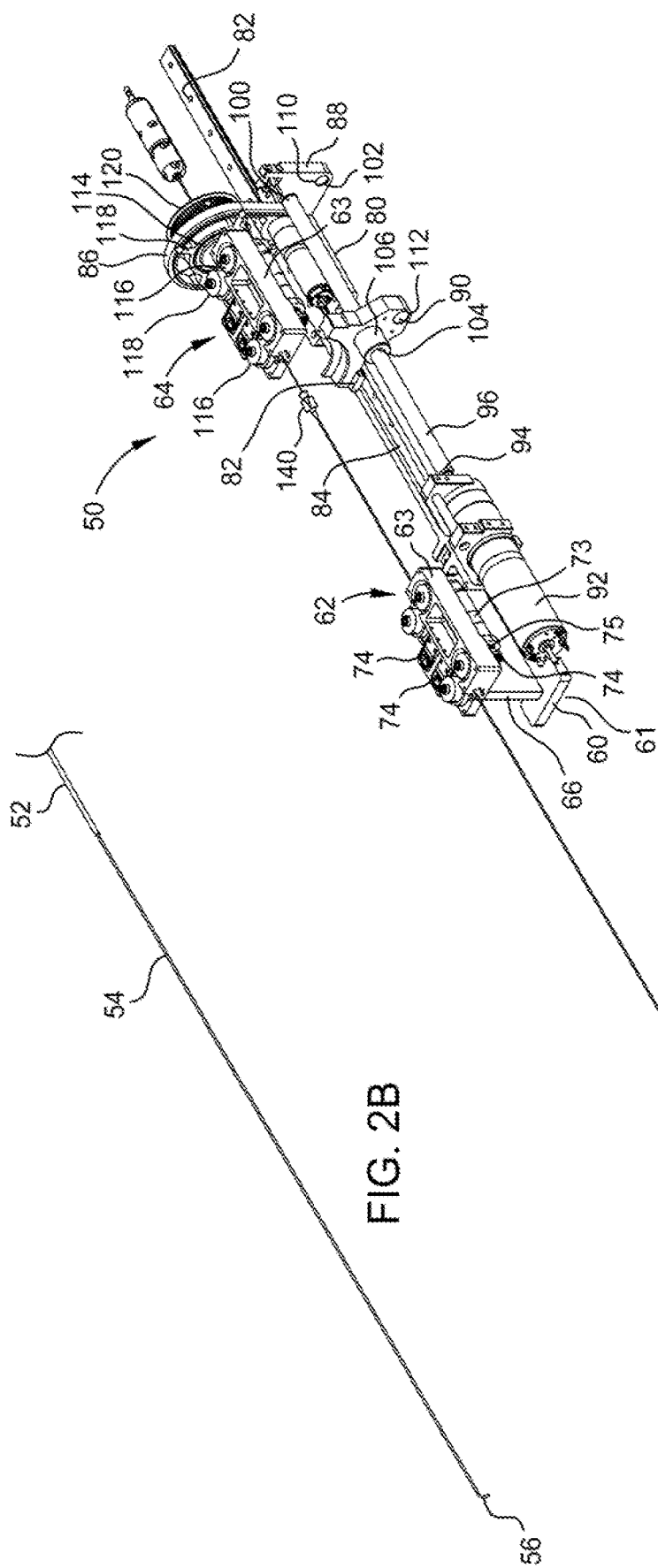

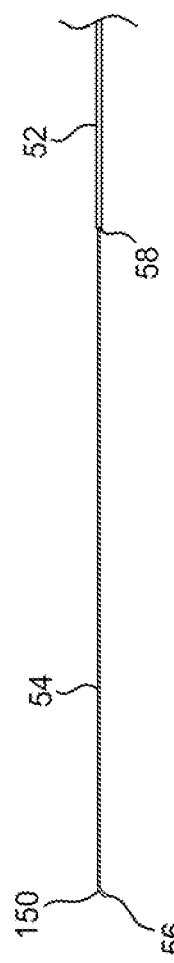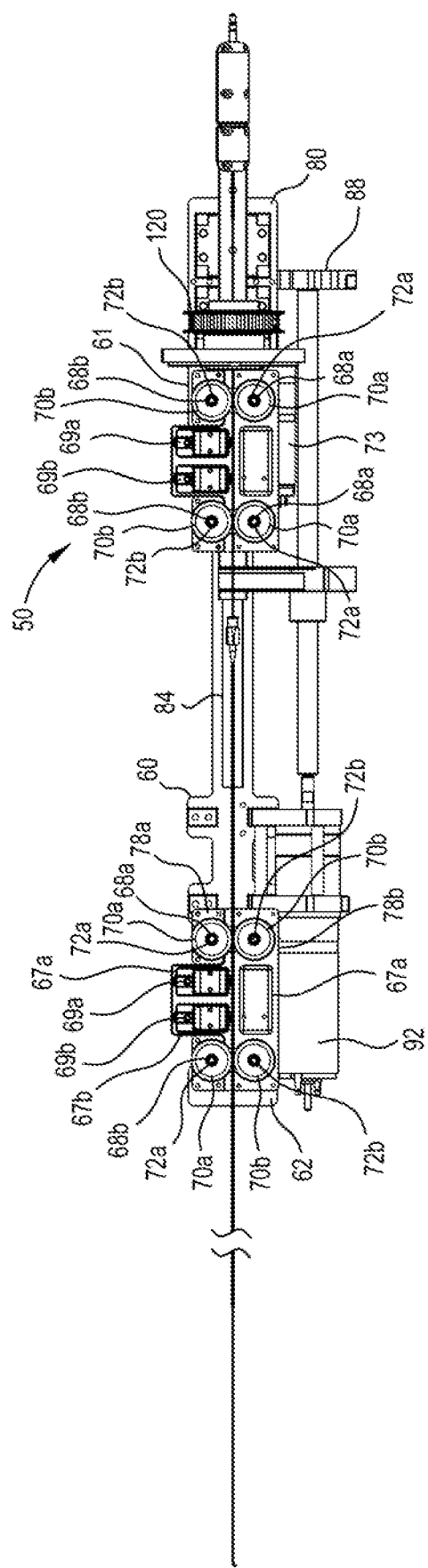

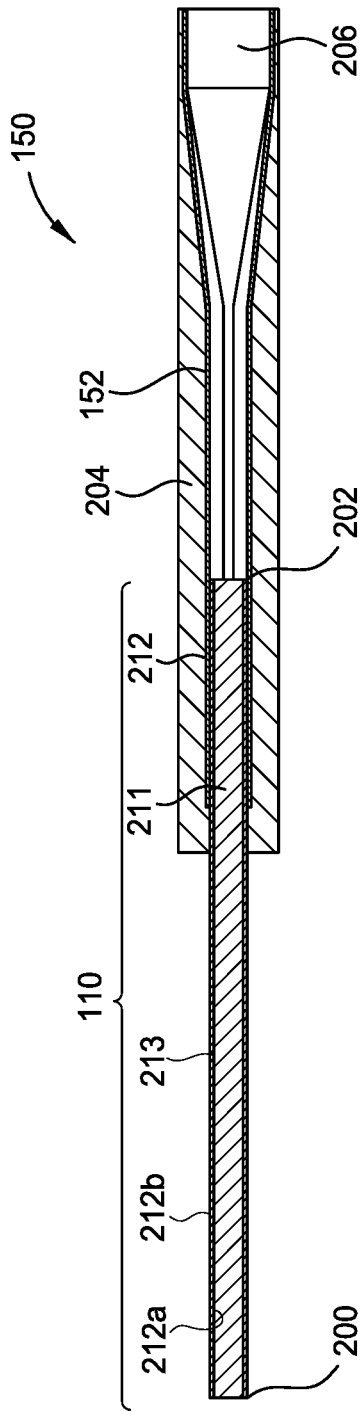
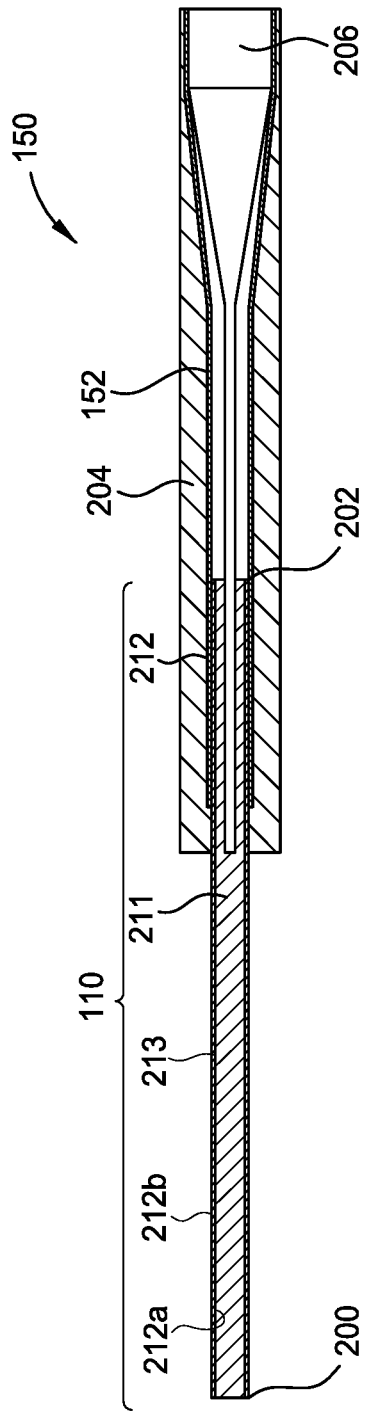

STEERABLE SURGICAL ROBOTIC SYSTEM

CROSS-REFERENCE TO RELATED APPLICATION

This application for Patent is a national stage application under 35 U.S.C. 371 of PCT/US2018/066811, filed Dec. 20, 2018, which claims benefit of U.S. Provisional Application No. 62/612,233, filed Dec. 29, 2017, entitled "STEERABLE SURGICAL ROBOTIC SYSTEM," which are both incorporated herein by reference in their entirety entireties.

BACKGROUND

Field

The present specification relates to the field of robotic medical procedures wherein a guidewire is introduced into a body through a catheter. More specifically, the present specification relates to the field of steerable surgical robotic systems for controlling the movement of the guidewire and the catheter in robotic surgery.

Description of the Related Art

Introduction catheters are known for delivering an element, such as a stent, a balloon, or other device to a desired location in a body lumen. In these applications, a guidewire is introduced into the body lumen, and steered to a desired location therein using a radiopaque marker on the end thereof which is visualized radiologically by a surgeon. This steering can include moving the orientation of the distal tip of the guidewire with respect to the remainder thereof, to steer the tip into tortuous portions of the lumen or into branch lumens, etc. Once the distal tip is properly positioned in the body, a sheath, which may include a deployable element such as the stent or balloon thereon or therein, is advanced over the wire to position the distal end thereof in a desired location within the patients' body.

There has arisen a desire to introduce such a catheter robotically, i.e., wherein an operator such as a surgeon controls a joystick or other control element connected to a controller, while viewing the tip of the guidewire and the patents' adjacent anatomy on a display screen. Robotic controllers used to advance a guidewire and guidewire independently within a patient are known. For example, in one such controller, a sheath within which the guidewire can be moved is advanced or retracted by a pair of rollers, and a guidewire is insertable thereinto from a location offset from the longitudinal axis of the sheath. As a result, it is not possible to easily control the relative motions of the sheath and guidewire, including the desirable ability to rotate the guidewire about its own axis to orient the tip thereof in a desired orientation for further advancement within a body, such as within a body lumen.

SUMMARY

Provided herein as a steerable surgical robotic system for positioning a catheter comprising a sheath and a guidewire within a patient body, including a sheath driver configured to advance and retract a sheath having a hollow interior along a sheath advance and retract path extending therein, and a guidewire driver configured to advance and retract a guidewire along a guidewire advance and retract path extending therein, wherein each of the sheath advance and retract path and the guidewire advance and retract path extend between pairs of rollers in the respective sheath and roller drivers, and the paths are parallel to each another.

BRIEF DESCRIPTION OF THE DRAWINGS

FIG. 2A is an isometric view of the robotic controller assembly shown in FIG. 1.

FIG. 2B is an isometric view of the distal end portions of the sheath and guidewire of FIG. 2A.

FIG. 3A is a plan view of the robotic controller assembly shown in FIG. 2A.

FIG. 3B is a plan view of the distal end portions of the sheath and guidewire of FIG. 3A.

FIGS. 9A and 9B are sectional views of a connection paradigm for electrically connecting electrodes on the bendable portion of the guidewire to a power source.

DETAILED DESCRIPTION

Figure 1:
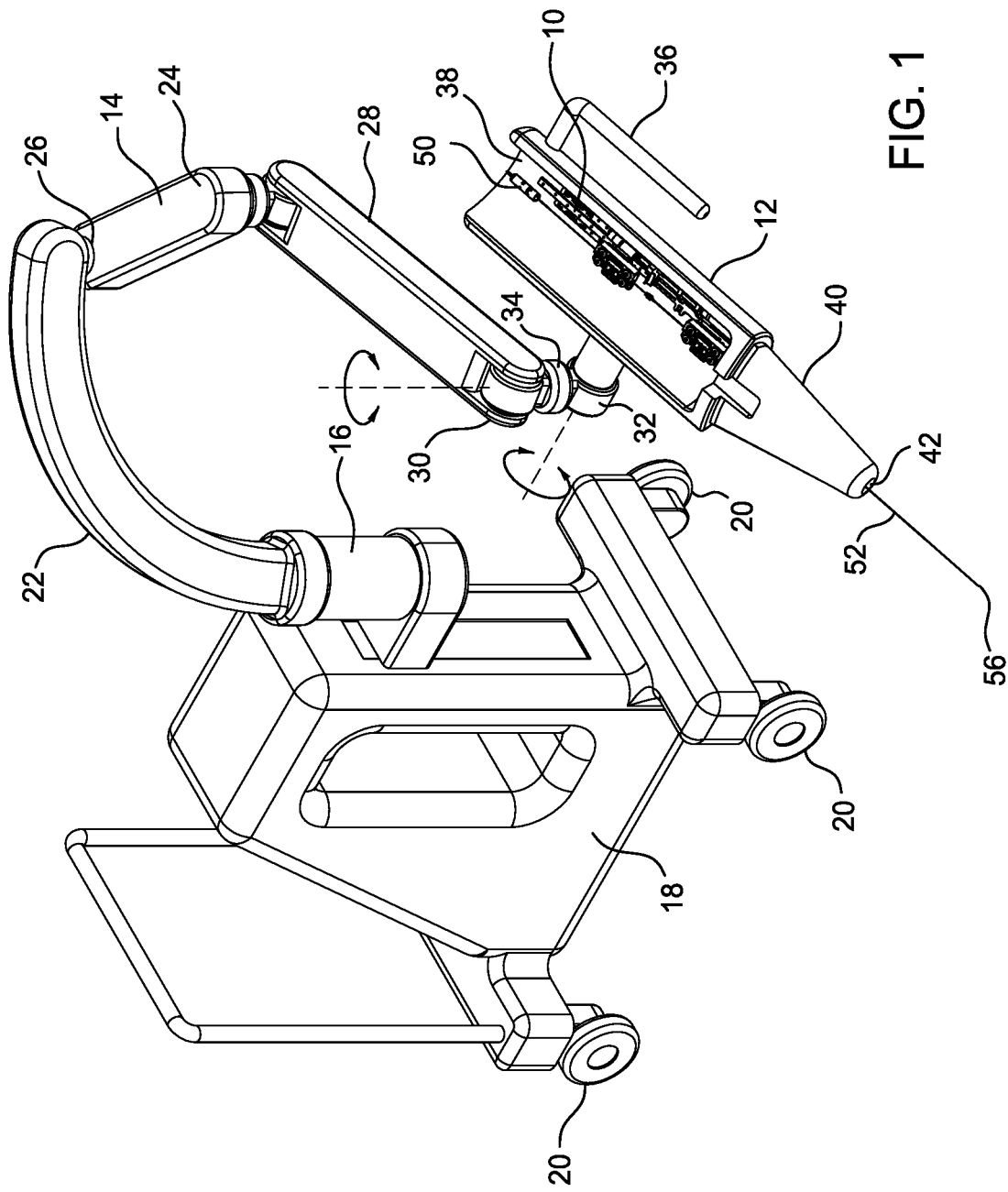
FIG. 1 is an isometric view of a service cart holding a robotic controller assembly of a steerable surgical robotic system having a steerable guidewire which can be inserted into a sheath and then fed, advanced and steered therethrough to the appropriate location within the body of a human or animal patient.

Herein, a steerable robotic system 10 is provided mounted in a guide tray 12 suspended from an arm 14 extending, in cantilevered fashion, from a base 16. Base 16 here is shown mounted on a moveable cart 18 which includes a plurality of lockable wheels 20, which allows a surgeon or other technician to move the cart 18 to a desired position adjacent to a patient, and lock the wheels 20 against movement, thereby locking the cart 18 in place. The base 16 is moveable translationally in a vertical direction with respect to the cart 18. The arm 14 here includes an arcuate cantilevered portion 22, a first sub arm 24 pivotally connected, and supported in a horizontal plane by, a swivel connection 26 to the cantilevered portion 22. A second sub arm 28 is likewise pivotally connected at a first end thereof to the first sub arm 24, and a right angled hanger 30 is pivotally connected to the opposite, distal end 30 thereof. The pivot connection of the second sub arm 28 to the first sub arm 24 allows controlled swinging motion of the distal end 30 of the second sub arm about an arc centered at the pivot connection of the second sub arm to the first sub arm 24, such that the distal end 30 may move upwardly or downwardly with respect to the supporting surface on which the wheels 20 of the cart 18 rest. A right angled support 32 is pivotally suspended from the distal end 30, and includes first and second portions connected at a further swivel 34, wherein the second portion is connected to the guide tray 12. Guide tray 12 is user positionable, via handle 36 thereon, with respect to the horizontal and vertical directions by virtue of the swivel connections of the arms 22, 24 and 28 and the right angle support 32. As a result, five degrees of freedom for positioning the guide tray 12 with respect to the cart 18 include 3 translational degrees of freedom, one pitch motion and one yaw motion.

A robotic controller 50, from which extends a flexible sheath 52, for example the outer sheath of a catheter, and a steerable guidewire 54 extending therein and ultimately therefrom (see, e.g. FIG. 2A), is located in and supported by the guide tray 12. The guide tray 12 includes a trough like support region 38 on which the robotic controller 50 is mounted and supported, and a funnel shaped shroud 40 extending from one end of the support region 38 and having a reduced diameter guide opening 42 at the tapering inwardly end thereof. The sheath 52, having the steerable guidewire 54 moveably disposed therein, extends from the robotic controller 50 and outwardly of the opening 42. The guide tray 12 is positionable with respect to a patient, and with respect to a desired orientation at which the sheath 52 extends inwardly into an incision in the patient, to allow the steerable guidewire 54 to reach a treatment site within a patients' body.

Herein, initially, the sheath 52 with the guidewire 54 therein is manually guided into the patient. A separate visual scope by which the distal end of the sheath 52 and guidewire 54 can be viewed, or radio-opaque markers on the distal ends of the sheath 52 and guidewire 54 can be combined with radiological imaging of the patient's body, to thereafter guide the distal ends of the sheath 52 and guidewire 54 to a desired location within a patient.

Figure 7:
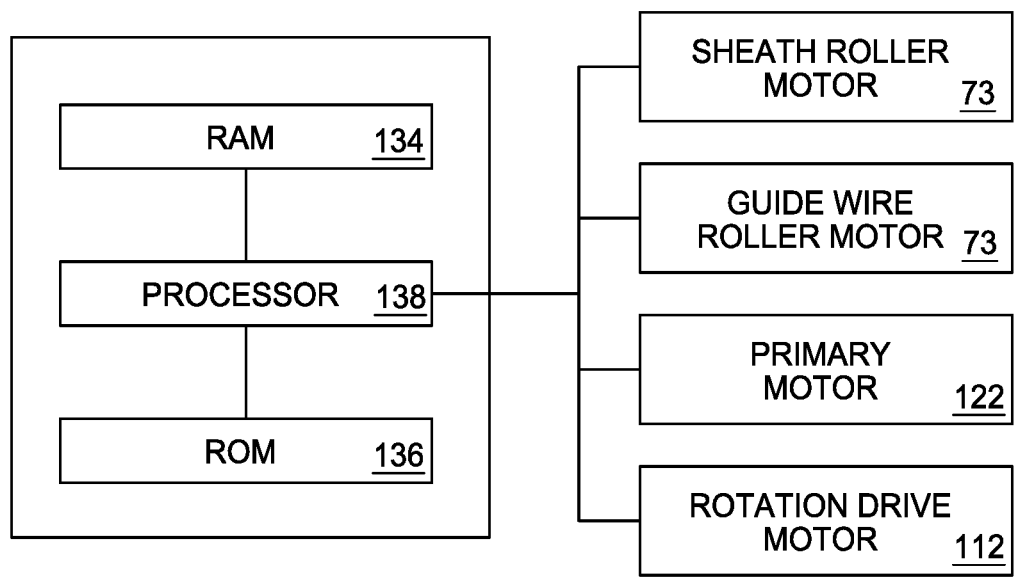
FIG. 7 is a block diagram of a controller architecture for controlling the operation go the robotic controller assembly.

Referring to FIGS. 2A and 3A, the robotic controller 50, having the sheath 52 and the guidewire 54 extending therefrom is, shown isometrically (FIG. 2A) and in plain view (FIG. 3A) In this construct of the robotic controller, the robotic controller 50 includes a sheath driver 62 and a guidewire driver 64, wherein the sheath driver 62 is fixedly connected to a the base 60 of the robotic controller fixed to the guide tray 12, and the guidewire driver 64 is slideably connected to the base 60. In this construct, each of the sheath driver 62 and the guidewire driver 64 are configured to enable fine movement control of the positioning of the guidewire 54 and sheath 52 with respect to the base 60, and the guidewire 54 is additionally moveably relative to the sheath 52 by moving the guidewire driver 64 slidably along the base 60. Thus, if each of the sheath driver 62 and guidewire driver 64 are held stationary with respect to each other, and they each simultaneously move the sheath 52 and guidewire 54 toward, or away from the opening 42 on the guide tray 12, the sheath 52 and guidewire 54 will not move with respect to each other despite moving with respect to the opening 42, and thus through the incision in the patient and thus within the a patient's body. Alternatively, where the sheath driver 62 moves the sheath 52 with respect thereto, the guidewire driver 64 may be itself moved, with the guidewire 54 remaining stationary with respect thereto, to effect simultaneous movement of the sheath 52 and guidewire 54 with respect to the opening 42, but not with respect to each other. In either case, as the guidewire is inserted into tortuous anatomy, the distal tip 56 of the guidewire 54 may also be controllably advanced away from,
or retracted toward or even into, the distal end 58 of the sheath 52, by operation of the sheath driver 62 and the guidewire driver 54 with a controller (FIG. 7).

The sheath driver 62 includes a base 61 fixedly supported on the end of a flange plate 66 extending generally perpendicular to the mounting base 60, and here the base 61 forms a roller housing 63 having two pairs of pinch roller assemblies 68a, 68b (FIGS. 3A, 3B). Each of the pairs of pinch roller assemblies 68a, 68b includes two rollers 70a, 70b, rotatably supported on drive shafts 72a, 72b extending generally perpendicularly to the drive path of the sheath 52 therethrough. One of the pair of drive shafts 72a, 72b of one of the pairs of rollers 70a, 70b, here shaft 72b of roller 70b of pinch roller assembly 68b, is coupled to a motor 73, here a motor having finely controllable arcuate movement of the output shaft 74 thereof, to enable small arcuate motions of the output shaft 74 thereof. The output shaft 74 is connected to a gear box 75 having a pair of conical or bevel gears, dedicated to drive the drive shaft 72b of the roller 70b of roller assembly 68b. Here, the centerline of the output shaft 74 is generally parallel to the drive path of the sheath 52, and the as the drive shafts 72a, 72b are generally perpendicular to that drive path, the pair of bevel gears transmit the rotation of the output shaft 74, while translating the direction of the centerline through which rotation occurs from parallel to the drive path to perpendicular to the drive path. To enable the pinching property of the pinch roller assemblies 68a, 68b, the drive shafts 72a of the rollers 70a are located on slidable housings 67a, 67b, and each slidable housing is spring loaded by a spring 69a, 69b or other biasing mechanism to push the outer circumferential surfaces of rollers 70a toward the corresponding outer circumferential surfaces of rollers 70b and thereby grip the sheath 52 extending therebetween. Because roller 70b or pinch roller assembly 68a is physically driven, the pinching of the sheath between rotating rollers 70a, 70b of pinch roller assembly 68b causes corresponding linear movement of the sheath captured therebetween, and the motion of the sheath 52 causes the rotation of the rollers 70a, 70b of pinch roller assembly 68b. Because the rollers 70a. 70b function as pinch rollers pinching the sheath 52 outer surface therebetween, only one of the two 70a, 70b of each pair 68a, 68b need be driven, and the other roller provides a follower roller surface. Alternatively, a second pair of bevel gears connected to a second output shaft of the motor 74, or a second motor and bevel gear set, can be provided to drive roller 70b of pinch roller assembly 68a.

The guidewire driver 64 is moveable linearly with respect to the sheath driver 62, and it also includes the same roller construct as that of the sheath driver 62. The guidewire driver 64 includes a base 80, including a lower slide portion 82 configured to be received within a slide bar recess 84 of the mounting base 60, an upwardly extending (in the direction away from the mounting base 60) rearward driver mount 86 and a forward side flange 90 extending therefrom. The mounting base 60 includes a side flange 88 extending generally parallel to the forward side flange 90. A primary motor 92, here a stepper motor or servo motor capable of controllable small angular movement of its output shaft 94 is coupled, through the output shaft 94, to a first end 98 of a threaded rod 96. The second end 100 of the threaded rod 96 is supported by a bearing (not shown) in an opening 102 of the side flange 88. The forward side flange 90 includes a threaded opening 104 therethrough, here a threaded opening 104 extending through a boss 106 extending from the primary motor facing side of the side flange 90 and aligned axially with the center of the shaft 94 and the opening 102 in the side flange 88. Stabilizer openings 110, 112 are provided through the flanges 88, 90 respectively, for receipt of a stabilizer bar (not shown) therethrough which is supported by the tray 12 or an additional element of the base to prevent arcuate motion of the side flange 90 about the output shaft 94 axis. The primary motor 92 is mounted to the mounting base 60 adjacent to the flange plate 66 and thus is fixed with respect to the position of the side flange 88. Thus, rotation of the primary motor 92, and thus the threaded rod 96 threadingly engaged with the threads in the boss 106, results in linear motion of the forward side flange 90 with respect to the side flange 88, and thus corresponding linear motion of the guidewire driver 64.

As previously discussed, the guidewire driver 64 has the same general construct as sheath driver 62, and includes the base 61 forming a roller housing 63 and two pairs of pinch roller assemblies 68a, 68b. Each of the pairs of pinch roller assemblies 68a, 68b includes two rollers 70a, 70b, rotatably supported on drive shafts 72a, 72b extending generally perpendicularly to the drive path of the guidewire 54 therethrough. One of the pair of drive shafts 72a, 72b of one of the pairs of rollers 70a, 70b, here shaft 72b of roller 70b of pinch roller assembly 68b, is coupled to a motor, here a motor 73 having finely controllable arcuate movement of the output shaft 74 thereof, to enable small arcuate motions of the output shaft 74 thereof. The output shaft 74 is connected to a gear box, dedicated to drive the drive shaft 72b of the roller 70b of roller assembly 68b. Here, the centerline of the output shaft 74 is generally parallel to the drive path of the sheath, and as the drive shafts 72a, 72b are generally perpendicular to that drive path, the pair of conical gears transmit the rotation of the output shaft 74, while translating the direction of the centerline through which rotation occurs from parallel to the drive path to perpendicular to the drive path. To enable the pinching property of the pinch roller assemblies 68a, 68b, the drive shafts 72a of the rollers 70a are located on slidable housings 67a, 67b, and each slidable housing is spring loaded by a spring 69a, 69b or other biasing mechanism to push the outer circumferential surfaces of rollers 70a toward their corresponding outer circumferential surfaces of rollers 70b and thereby grip the guidewire 54 extending therebetween. Because roller 70b or pinch roller assembly 68a is physically driven, the pinching of the guidewire 54 between rollers 70a, 70b of pinch roller assembly 68b causes corresponding linear movement of the guidewire 54 captured therebetween, and the motion of the guidewire 54 causes the rotation of the rollers 70a, 70b of pinch roller assembly 68b. Because the rollers 70a. 70b function as pinch rollers pinching the guidewire 54 outer surface therebetween, only one of the two 70a, 70b of each pair 68a, 68b of rollers 70a, 70b need be driven, and the other roller provides a follower roller surface. Alternatively, a second pair of bevel gears connected to a second output shaft of the motor 74, or a second motor and bevel gear set, can be provided to drive roller 70b of pinch roller assembly 68a.

Figures 4A, 4B:
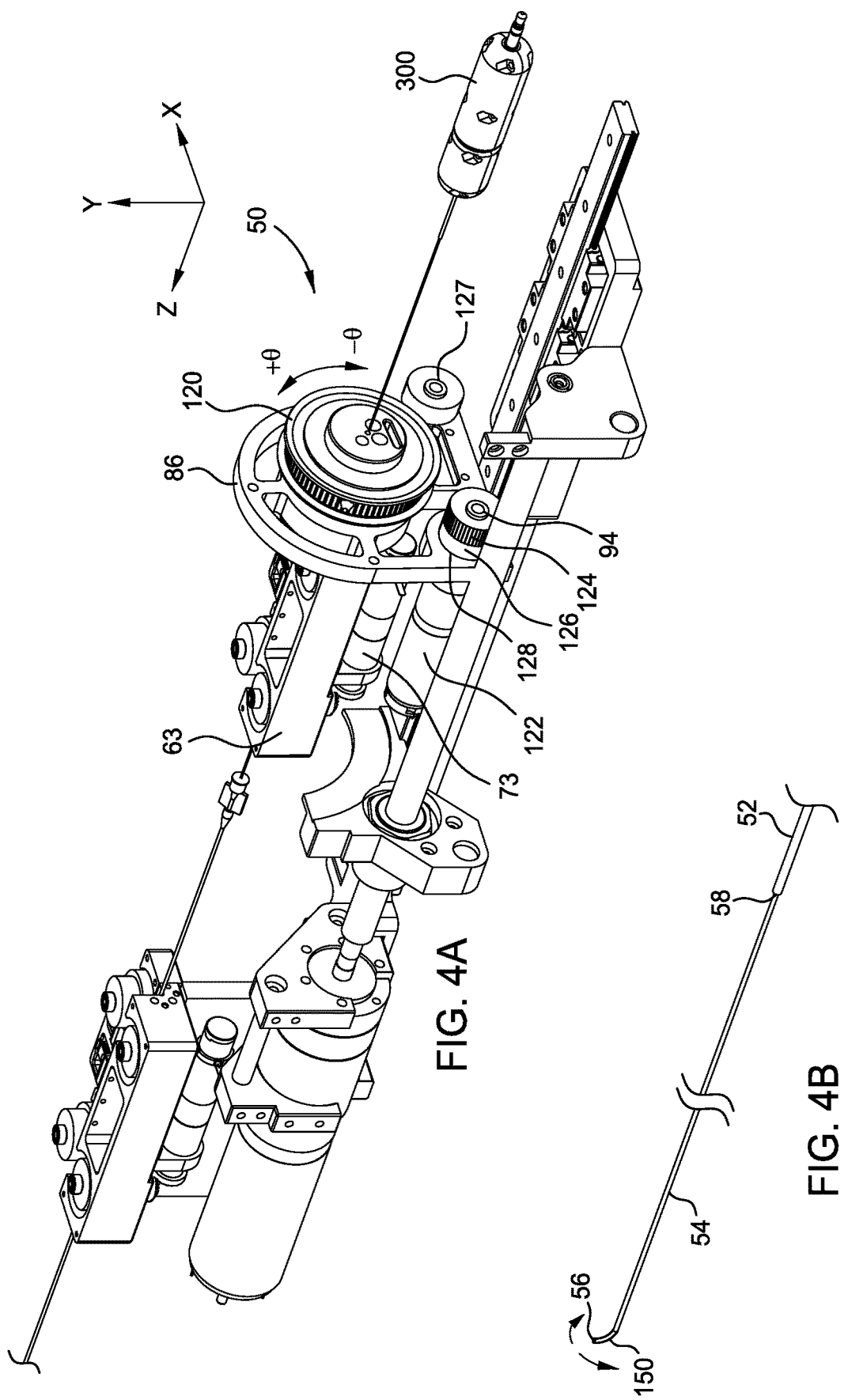
FIG. 4A is an isometric rear view of the robotic controller assembly shown in FIG. 2A.
FIG. 4B is a perspective view of the distal end portions of the sheath and guidewire of FIG. 4A.
Figures 5A, 5B:
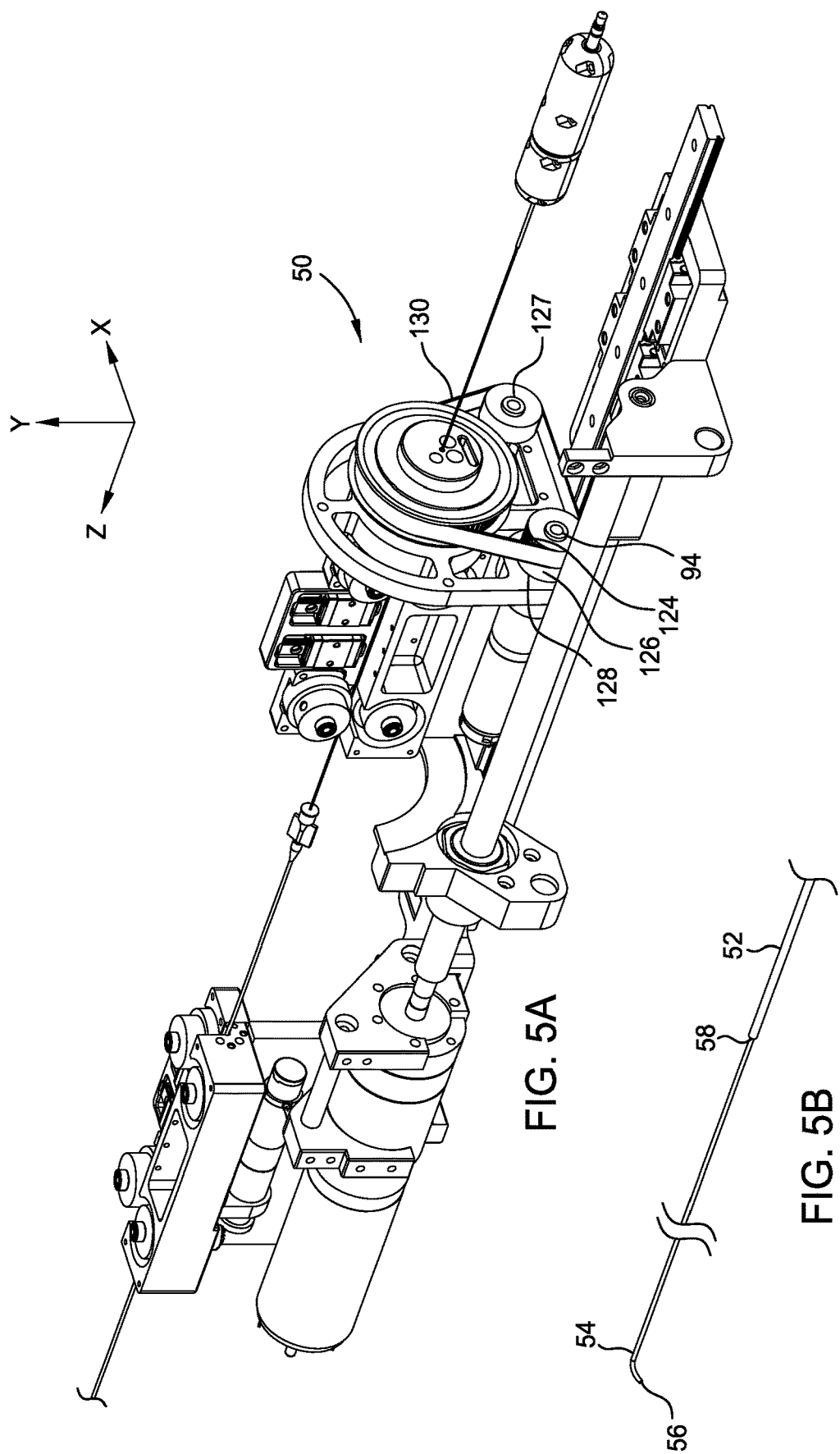
FIG. 5A is an isometric rear view of the robotic controller assembly shown in FIG. 4A, wherein the robotic controller has been actuated to rotate the guidewire with respect to the sheath.
FIG. 5B is a perspective view of the distal end portions of the sheath and guidewire of FIG. 5A.

In contrast to the base 61 of the sheath driver 62, the base 61 of the guidewire driver 64 is mounted at its rearward end 114 to a stub shaft 116 supported in a bearing 118 in driver mount 86, which in turn is connected to a timing gear 120. Referring to FIG. 4A, a rotation drive motor 122 is attached to the base 80, and a driving timing gear 124 is attached to the output shaft thereof which extends through, and is supported within a bearing 126 in, an opening 128 in the driver mount 86. An idler pulley 127 is also supported on a bearing in an opening in the driver mount 86. A timing belt 130 of FIG. 5A is extended around the timing gear 120, the idler pulley 127 and the driving timing gear 124, whereby motor operation causing the output shaft 94 thereof to rotate causes the timing belt 130 to move, causing rotation of the timing gear 120 in the +/−θ directions. This in turn causes rotation of the base 61 of the guidewire driver 64 to rotate along with the stub shaft about the stub shaft 116 axis. As the guidewire 54 is pinched between the rollers 68a, 68b, this rotational motion causes a corresponding rotation of the guidewire 54 within the guidewire driver 64. As shown in FIG. 4B, wherein the sheath driver 62 and guidewire driver 64 have the same orientation, the tip portion 56 of the guidewire here extends generally to the Y-axis along a curved portion extending from a portion of the guidewire 54 extending in the Z-direction. Without independently modifying the orientation of the tip 56 other than by rotating the base 61 portion of the guidewire driver 64 about the stub shaft axis to the position shown in FIG. 5B, the orientation of the tip portion 56 of the guidewire 54 now extends generally to the Y-axis along a curved portion extending from a portion of the guidewire 54 in the Z-direction.

Figure 6A:
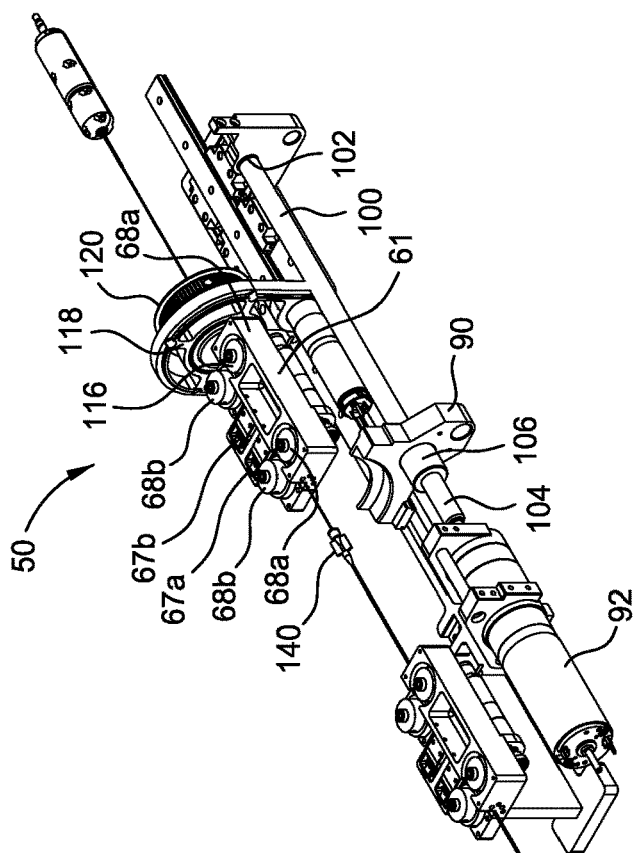
FIG. 6A is an isometric view of the robotic controller assembly of FIG. 2A, wherein the robotic controller assembly has been actuated, with respect to FIG. 2A, to change the relative positions of the sheath and the guidewire therein.
Figure 6B:
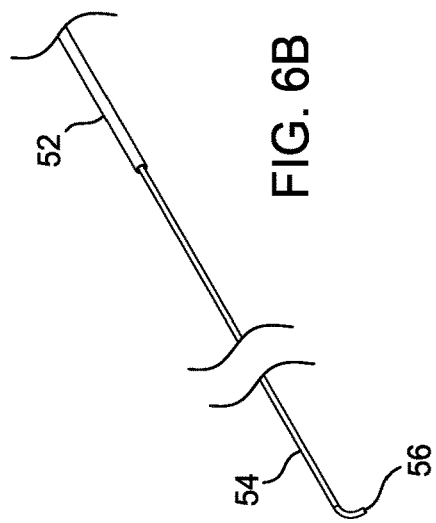
FIG. 6B shows that the sheath has moved to the left of the figure, while the guidewire position has remained stationary.

Herein, the driven rollers 70b and drive rollers 70a of the pinch roller assemblies 68a, b of each of the sheath driver 62 and guidewire driver 64 enable translational movement of the guidewire 54 and sheath 52, within the sheath driver 62 and guidewire driver 64, in the +/−Z direction of FIG. 4A. Additionally, the entire guidewire driver 54 is translationally moveable, in the Z direction, with respect the sheath driver 62, as shown by comparing their relative positions of FIGS. 4A and 5A with that shown in FIG. 6A. In FIG. 6A, operation of the primary motor 92 to rotate the threaded rod 96 attached thereto has caused the guidewire driver 64 to move toward the sheath driver 62 which is fixed to the base 60. As a result, if the driven roller 70b of the guidewire driver remains stationary, the guidewire 54 would be pushed inwardly of a ferrule 140 on the proximal end of the sheath 52 by which the guidewire 54 is introduced into the interior of the sheath 52. This could cause the region of the sheath 52 between the ferrule 140 and the sheath driver 62 to buckle. Therefore, the ferrule 140 may be physically connected (connection not shown) to the side flange 90 of the guidewire driver 64 and thus move translationally when the guidewire driver 64 is moved translationally. To effectuate this motion, the sheath 52 must be driven by driven roller 70b of the pinch roller assembly 68b of the sheath driver 62 at the same translational speed, and in the same direction, as the translational movement of the forward side flange 90. Also, comparing FIG. 2B to FIG. 6B, the translational motion of the forward side flange 90 from the position thereof in FIG. 2A to the position thereof in FIG. 6B shows that the sheath 52 has moved to the left of the figure, while the guidewire 54 position has remained stationary. This is accomplished by the controller operating the guidewire motor 73 to rotate the driven roller 70b of the pinch roller assembly 68b thereof to maintain the position of the guidewire 54 stationary, with respect to guide tray 12, and thus allow the sheath 52 to move with respect to the guidewire 54 therein and extending from the proximal and distal ends thereof.

Herein, the driving direction of the sheath 52 within the sheath driver 64, and the guidewire 54 within the guidewire driver 64, are fixed by the relative orientations of the sheath driver 62 and guidewire driver 64. In the implementation shown in, for example FIG. 2B, the guidewire 54 is pushed by the driven roller 70b and the remaining rollers pushing thereon directly into the ferrule at the proximal end of the sheath 52. In other words, the direction in which the guidewire is pushed by the roller is along the centerline of the interior volume of the sheath 52. Hence, when the guidewire is rotated by the guidewire driver, the portion thereof within the sheath 52, and extending from the distal end 58 thereof, will likewise rotate in the same direction. In contrast, in the prior device where the guidewire was introduced at an angle to the sheath, the guidewire will bend or loop exteriorly of the introduction location, and controllable rotation of the distal end of the guidewire there is erratic. Additionally, when the ferrule of the sheath 52 is physically secured to the side flange 90 of the guidewire driver 64, by proper operation of the rollers with respect to the relative movement of the guidewire driver 64 with respect to the sheath driver 62, the sheath 52 can be held taught between the side flange 90 and the rollers 70 of the sheath driver 62 to extend in a straight line path. Further, the rollers 70 of each of the sheath driver 62 and the guide wire driver can include detents therein aligned along the advancing/retracting direction of the sheath 52 or guidewire 54, to ensues the relative positions of the sheath 52 and guidewire 54 in their respective drivers 62, 64. This further ensures that the guidewire is unlikely to bend or loop outwardly when advance into, or rotated with respect to, the sheath 52 proximal end. By properly aligning the sheath driver 62 and guidewire driver 64 with respect to each other, the paths of the sheath and the guidewire through their respective drivers can be parallel, and collinear.

Referring to FIG. 7, a control system 132 of the robotic controller is shown schematically. The control system includes a programmable memory, including at least one random access memory 134 for temporarily storing a control program therein, a read only memory 136 within which operating parameters of the system and the control program are permanently stored, and a processor 138 configured to operate and control the robotic controller 50 using the control program. Hence, the controller is hard wired or wirelessly connected to the primary motor 122, and the motors driving the drive shafts 72b of the pinch roller assemblies 68b, to provide control signals thereto to allow selective advancing and retracting of the sheath 52 and the guidewire 54, as well as rotation of the guidewire 54, all under the control of the control system 132. This allows the various relative motions of the guidewire 54, the sheath 52, and the guidewire driver 64 and the sheath driver 62 hereof.

To properly position the distal end 58 of the sheath 52 in a patient lumen, the sheath 52, with the guide wire 54 extending therealong, is initially introduced into a patient incision, and advanced along a lumen while being radiologically imaged for viewing by the surgeon. This may initially be done manually, thereafter, the surgeon, while viewing the lumen, guidewire distal tip 56 and sheath distal end 58 radiologically, actuates a joystick or other device to control advancement, retraction, and rotation of the guidewire and the sheath concurrently or independently, as well as the bending orientation of the distal tip 56. As a result, the surgeon is able to direct the guidewire, and thus the sheath, to a desired location within a patient's body.

Figure 8B:
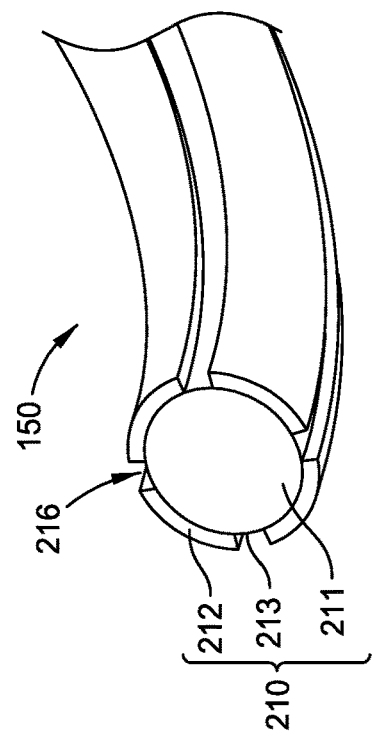
FIGS. 8A and 8B are isometric views of the bendable end of the guidewire on FIGS. 2A to 6A.
Figure 8A:
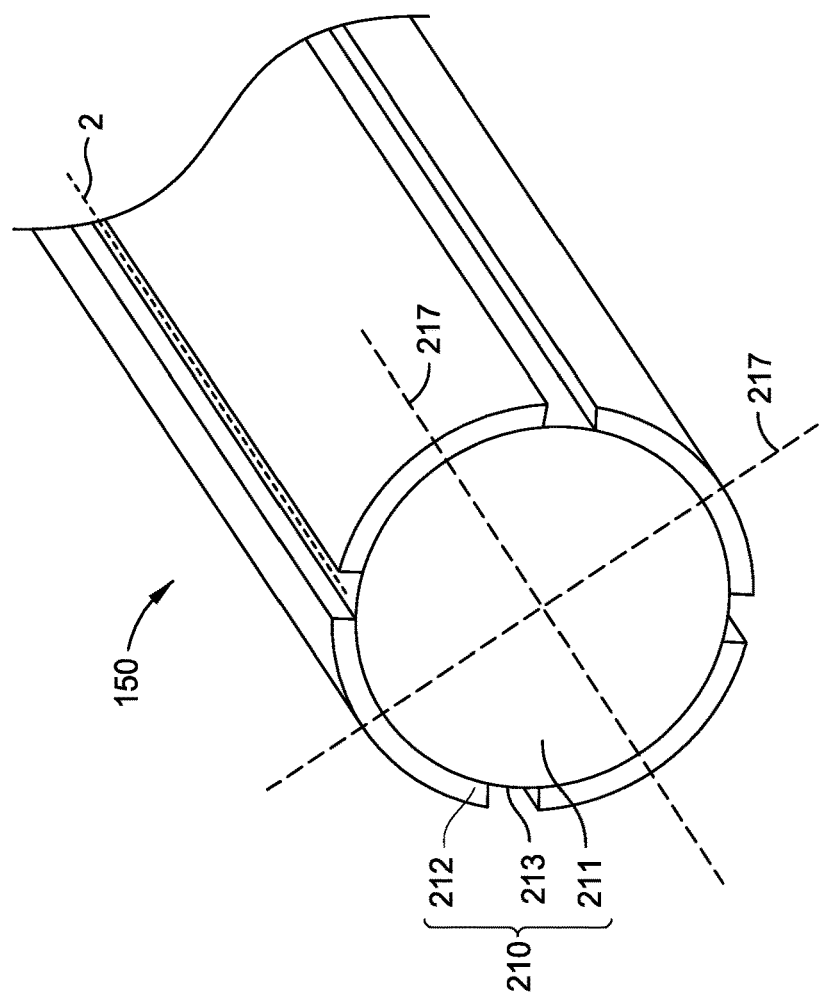

Here, to effectuate the transition of the orientation of the distal tip 56 of the guidewire between that shown in FIG. 1 to that shown for example, in FIG. 4B, the guidewire includes a bendable end portion 150. FIG. 8A is a perspective view of an embodiment of the bendable portion 150, illustrating the bendable portion 150 in the straight mode. The bendable portion 150 includes an ionic electroactive polymer actuator 210 comprising a polymer electrolyte layer 211 disposed adjacent to the distal end 200 of the guidewire 54 and disposed centrally within an angularly-distributed plurality of independently energizable electrodes 212 thereabout. Each of the plurality of electrodes 212 that together surround the exterior surface 213 of the polymer electrolyte layer 211 is connected to a distal end 123 of an electrically-conductive wire 152 (FIGS. 9A, 9B) through which an electrical signal or current may be supplied to the connected electrode 212. In one embodiment, the angularly distributed electrodes 212 are equi-angularly distributed about the exterior surface 213 of the polymer electrolyte layer 211. For example, but not by way of limitation, the ionic electroactive polymer actuator 210 may, in the embodiment of FIG. 8A, comprise four angularly-distributed electrodes 212 that are separated, at their centerlines, one from the others by about 90 degrees (1.571 radians). It will be understood that each of the plurality of electrodes 212 occupies a circumferential span along the surface of the polymer electrolyte layer, and that the "angular separation" may therefore be stated in terms of the centerlines 217 of the electrodes instead of in terms of the adjacent edges of the electrodes, which will be much closer to the adjacent edge of the adjacent electrode. In some embodiments, the electrodes are spaced in a manner to provide a substantial gap as insulation channels 216 intermediate adjacent electrodes. Selective application of current/voltage to one or more of the electrodes 212 causes the bendable portion 150 to move between the orientation thereof in FIG. 8A and that in FIG. 8B.

In one embodiment, the bendable end portion 150 of the guidewire 54 is configured as an ionic electroactive polymer actuator 210. In one embodiment, the ionic electroactive polymer actuator 210 includes a polymer electrolyte layer 211 made of PVDF-HFP that is impregnated with EMITF (as electrolyte). Alternately, other embodiments of the ionic electroactive polymer actuator 210 may include a polymer electrolyte layer 211 that includes at least one of a perfluorinated ionomer such as Aciplex™ (available from Asahi Kasei Chemical Corp. of Tokyo, Japan), Flemion® (available from AGC Chemical Americas, Inc. of Exton, Pa., USA), Fumapem® F-series (available from Fumatech BWT GmbH, Bietigheim-Bissingen, Federal Republic of Germany) or Nafion® (available from The Chemours Company of Wilmington, Del., USA.).

In one embodiment, the electrodes 212 may include one of platinum, gold, a carbon-based material, or a combination (e.g. a composite) thereof. In other embodiments, the carbon-material may include, for example, but is not limited to, carbide-derived carbon (CDC), carbon nanotube (CNT), graphene, a composite of carbide-derived carbon and the polymer electrolyte layer 211, and a composite of carbon nanotube and the polymer electrolyte layer 211. In an exemplary embodiment, as shown in FIG. 9, the electrodes 212 are double-layered, and include: a composite layer 212a of carbon (CDC and/or CNT) and PVDF-HFP/EMITF and a gold layer 212b thereover. The electrodes 212 can be integrated on the exterior surface 213 of the polymer electrolyte layer 211 using any suitable techniques. For example, but not by way of limitation, metal electrodes 212 can be deposited (e.g. platinum or gold electrodes) thereon using an electrochemical process. Alternatively, the double-layered electrodes 212 can be prepared and integrated on the exterior surface 213 by the following steps: spraying the composite layer on the exterior surface 213, spray coating a gold layer on the composite layer, followed by integrating both layers using a reflow process. The detail of the reflow process is discussed in PCT Application No. PCT/US17/16513, which is fully incorporated herein by reference in its entirety.

The bendable portion 150 can be selectively and controllably deformed to a bent mode by selective energization of one or more of the plurality of electrodes 212, as will be explained in further detail below. FIG. 8B is an isometric view of the portion of the bendable portion 150 of FIG. 8A in the deformed or bending mode. Each of the plurality of electrodes 212 is connected to a distal end 220 of the electrically-conductive wire 152 (FIG. 9A) through which an electrical signal may be applied to the electrodes 212 to which the wire 152 is connected, thereby causing metal cations within the polymer electrolyte layer 211 to move in a direction determined by the applied electrical signal. This cation migration produced by the applied electrical signal causes the polymer electrolyte layer 211 to swell in the portion of the polymer electrolyte layer 211 disposed proximal to the anode and to bend or warp in the direction of the remaining unswelled portion. As a result, the magnitude and the direction of bending deformation of the polymer electrolyte layer 211 of the ionic electroactive polymer actuator 210 can be controlled by strategically selecting the electrodes 212 to energize and by adjusting the electrical signal applied through the electrically-conductive wire 152 to those electrodes 212.

Alternately, in the event that the bendable portion 150 is observed to be in a deformed mode in the absence of the application of one or more electrical signals to one or more of the plurality of the electrodes 212, the magnitude of the observed deflection can be used to determine the magnitude and direction of an external force applied to the bendable portion 150 or, alternately, in the event that the application of a known current to the electrodes 212 fails to produce an anticipated deformation of the bendable portion 150, the difference between the anticipated deformation and the actual deformation (if any) can be used as an indicator of the magnitude of an external force applied to the bendable portion 150 of the guidewire 52.

Figure 8D:
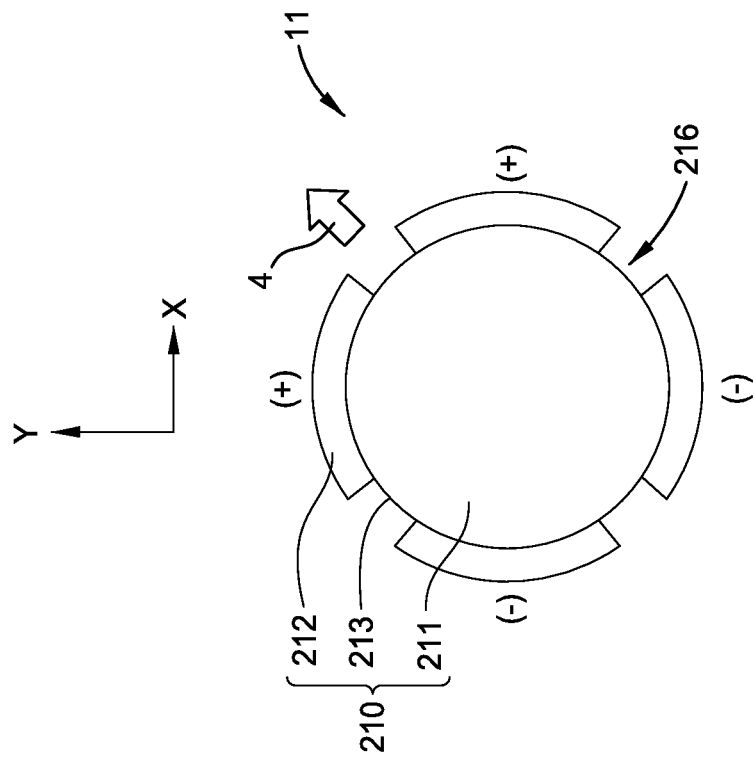
FIGS. 8C and 8D are end views of the guidewire.
Figure 8C:
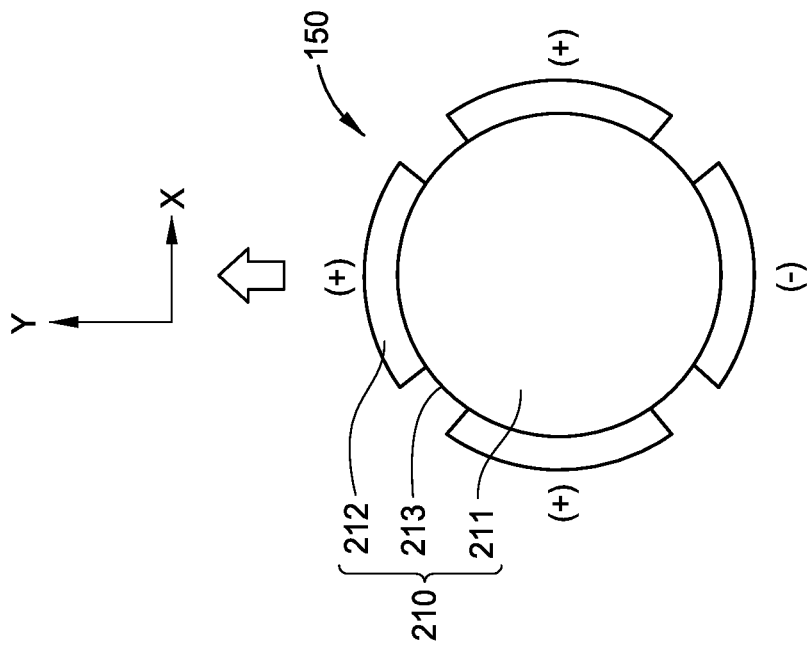

FIG. 8C is a cross-sectional view of the bendable portion 150 of FIGS. 8A and 8B illustrating one embodiment where a first selected set of four electrical signals is applied to four circumferentially distributed electrodes 212 disposed about the exterior surface 213 of the polymer electrolyte layer 211 to provide two degrees of freedom (e.g. bending along X-axis direction and/or Y-axis direction). FIG. 8C illustrates the electrical signals that may be applied to the plurality of angularly distributed electrodes 212 to impart bending of the bendable portion 150 in the direction of the arrow 3. It will be understood that the application of a positive charge (potential) on the electrodes 212 on the left and right sides of the bendable portion 150 of FIG. 8C, in addition application of a positive charge (potential) to the electrode 212 at the top of FIG. 8C, and further in addition to the application of a negative charge (potential) to the electrode 212 at the bottom of FIG. 8C, may result in a different amount of deformation than would occur as a result of the application of a positive charge (potential) on the electrode 212 at the top of FIG. 8C with a negative charge (potential) imparted to the remaining electrodes 212. It will be understood that the user may select the plurality of electrical signals that produces the deformation desired by the user.

FIG. 8D is the cross-sectional view of the bendable portion 150 of FIGS. 8A and 8B revealing another embodiment that a second selected set of four electrical signals applied to the circumferentially distributed electrodes 212 disposed about the polymer electrolyte layer 211. FIG. 8D illustrates the application of a positive charge (potential) to the electrode 212 at the top of the bendable portion 150 of FIG. 8D and also to the electrode 212 at the right side of the bendable portion 150 of FIG. 8D, and FIG. 8D further illustrates the application of a negative charge (potential) to the electrode 212 at the bottom of FIG. 8D and also to the electrode 212 at the left side of FIG. 8D. The deformation of the polymer electrolyte layer 211 results from the application of these electrical charges (potentials) is in the direction of the arrow 4.

It will be understood from FIGS. 8C and 8D that the bendable portion 150 can be bent in multiple directions and with varying degrees of deformation or deflection by strategic control of the sign (+, −) and magnitude of the electrical charges imparted to each of the individual electrodes 212. Although the embodiment illustrated in FIG. 8A to 8D illustrates a bendable portion 150 including four electrodes 212, it will be understood that the bendable portion 150 of the guidewire 54 may include fewer than four or more than four electrodes 212, and such other embodiments will have differing deflection and deformation directional capacities and thus provide more or less degree(s) of freedom.

The electrically-conductive wires 152 can be interconnected with the electrodes 212 in various configurations using any suitable connecting technique. For example, conducting paste or laser welding can be employed to physically and electrically connect the electrically-conductive wires 152 and the electrodes 212. FIGS. 9A and 9B shows a cross section of the ionic electroactive polymer actuator 210 illustrating one embodiment of physical and electrical connection of the electrically-conductive wires 152 and the electrodes 212, which is disclosed in Provisional Application No. 62/539,346 and fully incorporated herein by reference in its entirety. Here, electrically-conductive wires 152 are interconnected with at least a portion of each of the electrodes 212 (e.g. being integrated (see e.g. FIG. 9A) or embedded (see, e.g. 9B)) at the proximal end 202 of the ionic electroactive polymer actuator 210 using conducting paste or laser welding. Then, a polymer sleeve 204 is provided to facilitate guidewire maneuverability within a body lumen or passage. The polymer sleeve 204 is overlaid on a guidewire core 206, a portion of the proximal end 202 and the electrically-conductive wires 152 connected thereto, to firmly secure them together.

The proximal end of the guidewire 54 is further coupled to a connector 300 (see e.g. FIG. 4A) that can be further electrically connected to an electrical controller (not shown). The electrical controller is configured to selectively control the electrical charges carried by the electrically-conductive wires 152 and impart to the plurality of electrodes 212 to manipulate and steer the bendable portion 150 of the guidewire. In some embodiments, the electrical controller may comprise a processor (not shown) that calculates the values of an electrical signal applied to the electrodes, in response to a user's input signals from the master controller (not shown). The master controller may include, for example, a joystick for enabling the user to input the bending control signals to the electrodes 212 of the bendable portion 150 for providing two degrees of freedom of bending through the electrical controller.

Herein, there are provided mechanisms for localized manipulation of the distal tip 56 of the guidewire 54 using an electroactive polymer and electrode construct, as well as the ability to advance the distal tip 56 with respect to the distal end 58 of the surrounding sheath 52, as well as the ability to rotate the guidewire 54, and thus move the distal tip in a circular pat, the radius of which is dependent upon the bending thereof resulting from the use of the electroactive polymer and electrodes to cause distal tip 56 motion with respect to the remainder of the guidewire 56. Thus, in use by a surgeon, the distal end 58 of the sheath is first introduced into a patient, such as into a body lumen of a patient. Here, the portion of the sheath 52 adjacent the distal end 58 includes one or more radioactive markers, allowing the distal end to be radiologically imaged within a body lumen. Then, as tortuous lamed architecture is encountered, the distal tip 56 of the guidewire 54, which is also radioactively marked, can be advanced with respect to the distal end 58 of the sheath 52, by operating the motor 73 of the guidewire driver 64 to cause at least one roller 70 thereof to rotate causing advancement of the guidewire with respect to the distal end 58 of the sheath 52. While the guidewire 54 is advancing, the surgeon, by operation of a joystick or other device connected to the controller, can control the advance of the guidewire 54, control the bending directional and amount of the bending t caused by the operation of the electrodes and electroactive polymer as a result of the controller electrically powering selected ones of the electrodes 212, and also, once the bending of the guidewire 54 end is achieved, move the distal tip along an arc to align it with a further portion of, or branch of, the lumen, followed by advancement of the distal tip 56 into the further portion or branch of the lamed. The sheath 52 can then be advanced along the guidewire, if required, and the sequence of operations repeated until the distal end of the sheath is positioned at a desired location in the patients' body.

The distal end of the sheath may, for example, carry a stent, a balloon, or other deployable device. Thus, when the distal end of the sheath has been advanced to the desired lumen location, the stent or balloon may be deployed, and the sheath 52 and guidewire removed from the patient.

What is claimed is:

1. A robotic controller for positioning a catheter comprising a sheath having a hollow interior, and a guidewire, within a patient body, comprising;
    a base;
    a sheath driver including a sheath advance and retract path extending therein and a sheath driver roller housing fixedly connected to the base and configured to advance and retract the sheath along the sheath advance and retract path extending therein, the sheath driver roller housing further comprising at least one pair of sheath rollers, the sheath rollers of the pair of sheath rollers disposed to face one another along the sheath advance and retract path, each sheath roller comprising an outer circumferential surface configured to grip the sheath when the sheath is positioned between the sheath rollers;
    a guidewire driver including a guidewire advance and retract path extending therein and a guidewire driver roller housing moveably connected to the base and configured to advance and retract the guidewire along the guidewire advance and retract path extending therein and to selectively move toward and away from the sheath driver, the guidewire driver roller housing further comprising at least one pair of guidewire rollers, the rollers of the pair of guidewire rollers disposed to face one another along the guidewire advance and retract path, each guidewire roller comprising an outer circumferential surface configured to grip a guidewire when a guidewire is positioned between the guidewire rollers, and the guidewire driver further including a driver mount and the guidewire driver roller housing being rotatably coupled to the driver mount operatively fixedly coupled to a slide bar moveably received in a slide bar recess; wherein
    each of the sheath advance and retract path within the sheath driver roller housing and the guidewire advance and retract path within the guidewire driver roller housing extend between pairs of sheath rollers and guidewire rollers in the respective sheath and roller drivers, and the sheath advance and retract path and the guidewire advance and retract paths are parallel to each another.

2. The robotic controller of claim 1, wherein the sheath advance and retract path and the guidewire advance and retract are aligned in a collinear relationship with each other.

3. The robotic controller of claim 1, wherein the guidewire driver further includes a driver mount and the guidewire driver roller housing is rotatably coupled to the driver mount operatively fixedly coupled to a slide bar moveably received in the slide bar recess.

4. The robotic controller of claim 3, wherein the guidewire driver further comprises a ferrule on a proximal end of the sheath extending from the sheath driver.

5. The robotic controller of claim 3, wherein
    the guidewire driver further comprises a side flange having an opening therein and a forward side flange having a threaded opening extending therethrough, and
    a primary motor is connected to the base, and a threaded rod extend therefrom, wherein the threaded rod extends through and is threadingly connected to the threaded opening in the forward side flange, and an end of the threaded rod distal to the motor is received in the opening in the side flange.

6. The robotic controller of claim 3, wherein the pairs of rollers in the guidewire driver roller housing include a first pair of rollers and a second pair of rollers, and each of the first and second pairs of rollers include a driven roller coupled to a roller drive shaft connected to a roller drive motor.

7. The robotic controller of claim 6, wherein the guidewire driver further comprises:
    a rotation motor coupled to a driving gear;
    a rotation gear;
    a belt coupled to the rotation gear and the driving gear; and
    a support shaft extending through, and rotatably supported in the driver mount, the support shaft extending between and coupled to the rotation gear and the guidewire driver roller housing.

* * * * *